United States Patent
Schukin et al.

(10) Patent No.: US 6,858,000 B1
(45) Date of Patent: Feb. 22, 2005

(54) DEVICE FOR TREATING TISSUES WITH AN ELECTROMAGNETIC FIELD

(75) Inventors: Sergei Igorevich Schukin, Moscow (RU); Aleksandr Alekseevich Morozov, Moscow (RU); Vyacheslav Grigorievich Zubenko, Moscow (RU); Gennady Ivanovich Semikin, Moscow (RU); Oleg Stepanovich Naraikin, ul. 26 Bakinskikh Komissarov., 6-22-115, 117526, Moscow (RU)

(73) Assignees: Olga Pavlovna Barysheva, Moscow (RU); Oleg Stepanovich Naraikin, Moscow (RU); Victor Frunzevich Tarkhov, Moscow (RU); Sergei Frunzevich Tarkhov, Moscow (RU)

( * ) Notice: Subject to any disclaimer, the term of this patent is extended or adjusted under 35 U.S.C. 154(b) by 98 days.

(21) Appl. No.: 10/169,219
(22) PCT Filed: Feb. 22, 2001
(86) PCT No.: PCT/RU01/00075
§ 371 (c)(1),
(2), (4) Date: Jun. 25, 2002
(87) PCT Pub. No.: WO02/04070
PCT Pub. Date: Jan. 17, 2002

(30) Foreign Application Priority Data

Jul. 10, 2000 (RU) ........................................ 2000118668

(51) Int. Cl.$^7$ .............................................. A61N 1/00
(52) U.S. Cl. ..................................................... 600/13
(58) Field of Search ................. 600/9–15; 607/100–103

(56) References Cited

U.S. PATENT DOCUMENTS 5,453,074 A * 9/1995 Imoto ........................... 600/15

6,155,966 A * 12/2000 Parker ........................... 600/13

FOREIGN PATENT DOCUMENTS

WO        WO 9110875 A1 * 3/1997    ............ A61N/2/00

* cited by examiner

Primary Examiner—Samuel G. Gilbert
Assistant Examiner—Nikita R. Veniaminov
(74) Attorney, Agent, or Firm—Garrison & Associates PS; David L. Garrison

(57) ABSTRACT

The invention relates to of medicine and medicine equipment and concerns techniques and means for medicinal action with electromagnetic fields to living tissues. A method provides a stimulating effect of an electromagnetic field to metabolic processes in tissues of an organism, that result in positive shifts of a functional state of regulatory systems. On a contactless electromagnetic action to members of a vascular system, biomechanical, bioelectrical and bioresonant processes in the vascular system control the tone of a vascular wall with a high degree of selectivity. The method and device allow to reduce treatment periods, post-operative and other types of rehabilitation due to a deep contactless interaction of biological tissues of a patient, provided by sensor fields of the organism at an information level, with low-frequency electromagnetic fields that are created by the inventive device with special bioadequate parameters relative to dynamic (that is, time and shape parameters), amplitude and geometric-spatial properties. The inventive device consists of a specialized biosynchronized generator of low-frequency electrical signals that arrive at an electromagnetic inductor converting the electrical signals into electromagnetic fields having given electromagnetic properties determined as a result of fundamental theoretical studies and experiments.

10 Claims, 1 Drawing Sheet

DEVICE FOR TREATING TISSUES WITH AN ELECTROMAGNETIC FIELD

TECHNICAL FIELD

Figure 1:
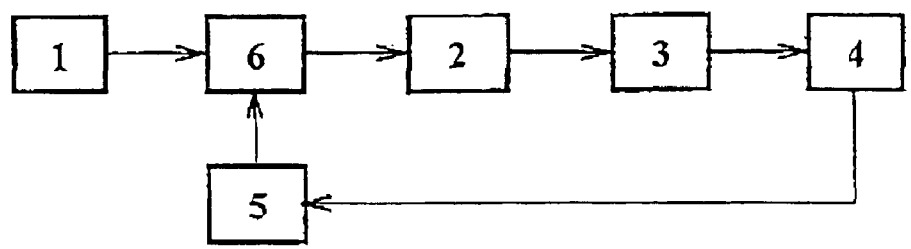

The invention relates predominantly to the art of medicine and medicine equipment and concerns techniques and means for medicinal action with electromagnetic fields to living tissues. It also can be used in veterinary and during scientific biological studies.

BACKGROUND ART

Electromagnetic fields are the basic factor of the most physiotherapeutic procedures aimed at normalising the functions of organs and tissues disturbed for that or other reasons, and are the most widely used in medical practice. There are tens of methodology and scheme variants for medicinal action of electromagnetic fields to a human organism, said variants being developed for recovering disturbed functions of separate organs.

For example, known is a method for treatment of cerebral vascular diseases of artherosclerotic nature, comprising the steps of acting to a region of an affection nidus in cerebrum with an electromagnetic field having a frequency of 50 Hz and an intensity of 90 to 250 Oe. The observed improvement in hemodynamics is implied by increasing the linear velocity of blood flow and the blood volume of cerebral vessels, normalising the tone of a vascular wall, decreasing the events of venous stagnation (USSR Inventor's Certificate 942,776, A 61 N 2/04, 1982).

Disclosure has been made of a method for treatment of the postoperative hepatic insufficiency by preventing the blood stagnation in the portal region of spleen, comprising the steps of acting to the liver artery with an electromagnetic field having a frequency of 80 to 100 Hz in the systolic phase of heart activity, and 800 to 1000 Hz in the diastolic phase. Currents having the frequency of 80 to 100 Hz act to the sympathetic nervous system, cause relaxation of smooth muscles and reduction of the pressure in the proper hepatic artery. Currents having the frequency of 800 to 1000 Hz act to the parasympathetic nervous system, cause drastic increase of the tone of smooth muscles and increase of the pressure in the proper hepatic artery (USSR Inventor's Certificate 1,147,408, A 61 N 1/18, 1985).

In case of thrombosis of blood vessels, it is possible to act to this region with electromagnetic fields in the radio frequency range (200 to 500 Hz) at a field power of 0.1 to 10 W (International Application WO 97/10875, A 61 N 2/00, 1997).

Improvement in the blood supply for organs and tissues, that allows to reduce pain syndromes of different localisation, can be achieved by placement of a belt comprising a series of variable electromagnetic field sources at a patient's body (European Application 0 160 703, A 61 N 1/42, 1985).

To improve the regional blood circulation in a pathologic zone during treatment of the long compression syndrome, it has been proposed to effect a sequential action with electromagnetic fields having different amplitudes and time characteristics, exactly, it has been recommended to act to an originally affected tissue with a field having an induction of 2.5 to 1.2 mT and a frequency of 0.8 to 2.5 Hz during 15 to 20 minutes, then to act with a field having an induction of 3.0 to 4.0 mT and a frequency of 2.2 to 3.0 Hz during 25 to 35 minutes. In such the mode of action, optimum removal of the arterial vessel spasm and normalisation of the tone of venous vessel walls were achieved. In doing so, a shape of impulses within said frequency and amplitude parameters corresponds to a symmetrical exponential impulse of current in a solenoid system having a current impulse rise to drop front ratio of 50+10% (RF Patent 2,019,209, A 61 N 2/04, 1994).

In stomatology, to treat soft tissues of the prosthetic bed, there are the steps of acting to the face skin in a region of projecting a disturbed tissue section thereto with an electromagnetic field having an impulse recurrence rate of from 3 to 30 Hz, a modulation frequency of from 0.3 to 0.8 Hz and a width of a harmonic component spectrum of from 500 Hz to 1 kHz, followed by increasing the impulse recurrence rate of the electromagnetic field increases to 80 to 120 Hz, and continuing the action.

Selection of the parameters of action is implied by that the impulse recurrence frequencies in the range of from 3 to 30 Hz are adequate to a living organism, the action spectrum width in the range of from 500 Hz to 1 kHz is the most probable frequency range allowing to regulate exchange processes in living tissues, the modulation frequency within from 0.3 to 0.8 Hz allows to provide the comfort state to a patient by generating the pauses even at the impulse recurrence rate greater than 30 Hz.

To individualise the treatment, the parameters of a natural electromagnetic field of a tissue are preliminary determined at a test section of the face skin of a particular patient in an exit region of the trifacial nerve face branch, said field being provided by vitality of the tissue, and, prior to the next action, and the electromagnetic field having respective parameters is generated for subsequent action (RF Patent 2,119,360, A 61 N 2/00, 1998).

To accelerate the healing of bone fractures and eliminate the disturbances of blood circulation, it was recommended to act to a living tissue with an electromagnetic field created by unipolar rectangular impulses having an impulse recurrence rate of 0.1 to 100 Hz and an amplitude of 0.1 to 15 V. A device to be used provides the presence of an offset circuit that prevents the impulses of opposite polarity from being present when a magnetic flux drops due to the drop of a generated impulse (European Application 0 181 053, A 61 N 1/42, 1986).

Disclosure has been made of a method and a device for non-invasive local action with electromagnetic fields to the blood flow at a selected region by applying one or two electromagnetic coils generating electromagnetic fields in this region. This method implies using the non-invasive ultrasonic echo Doppler checking of propagation of an impulse wave through the selected region, and calculating the changes in a wave propagation velocity as a criterion of the electromagnetic field action to be effected. The method is capable of selectively changing the flow circulation dynamics at least in the region of action. In doing so, the shape of impulses is asymmetrical and contains a pulsing signal component. However, quantitative parameters of used electromagnetic fields were not recited (European Patent 0 145 173, A 61 N 1/42, 1984).

It has been patented a device for action to biological functions of living tissues with an impulsed electromagnetic field, said device being intended to transfer ions from electrolytic liquids of a body into and through vessel walls and membranes surrounding them. The device provides action of an electromagnetic field having parameters selected such that the energy induced by said field in an electrolytic liquid is greater than the heat energy and is within an amplitude window peculiar to cells, wherein a basic current impulse consists of a current signal of rectangular shape and a current superposed to each other, said current increasing according to the exponential law, with a subsequent interval having a not less duration; a basic frequency of the basic current impulse is from 100 to 1000 Hz; an amplitude of a basic impulse sequence is modulated by a frequency of from 0.5 to 35 Hz; the modulated basic impulse sequence is transmitted as a series of impulses during 0.3 to 1.0 sec followed by a pause during 5.0 sec.

It is possible to optimise the action to an organism by selecting the field parameters, preferably, using a biological feedback. In particular, it is possible to measure the blood pressure and regulate the action after achievement of an optimum value of said pressure. A device includes a signal shaper comprising a low frequency current impulse generator to whose output a transmission antenna is coupled, and the device is capable of creating electromagnetic fields having recited characteristics (RF Patent 2,093,213, A 61 N 2/04, 1997).

Known are a method and a respective device intended to stimulate the central and peripheral nervous system for therapeutic purposes, said method and device providing the action of an electromagnetic field to a local region of a body, said field being formed of a combination of point fields created by individual coils and electrodes arranged within a zone action (European Application 0 709 115, A 61 N 2/00, 1996).

Disclosure has been made of an apparatus for treatment of diseases or states associated with hyperaemia of tissues, preferably of extremities, said method providing the possibility to apply a magnetic field to a zone of action transversely to the basic direction of blood vessels, and to apply an electric field transversely to the direction of the magnetic field, as a result of which electrically charged blood particles, such as ions, obtain a spiral-shaped rotary motion, and the flood flow in a tissue is amplified (International Application WO 82/01135, A 61 N 1/42, 1982).

Disclosure has been made of an apparatus and a method for treating virus and genetic diseases, based on action to an affected biological material, for example, a gene or a virus, with electromagnetic fields having an energy density and an impulse recurrence rate that are determined as a function of the mass of an object subjected to said action. The field energy is selected as equal to the gravitation energy of the affected biological material in order to provide achievement of a resonance mode. The procedure is performed in an aqueous medium into which a solenoid is immersed in whose interior a magnetic field is created (European Application 0 371 504, A 61 N 2/04, 1990).

To act to pathologic cells, there have been developed a method and an apparatus whose principle of operation consists in applying electromagnetic fields having an intensity of from 1 to 30 mT, and extremely low-frequency electromagnetic fields having a frequency of from 1 to 1000 Hz, said fields being control fields (European Application 0 966 988, A 61 N 2/02, 1999).

Disclosure has been made of multiple embodiments of a combined medicinal action of electromagnetic fields and other physical factors.

It has been patented a method for treatment of diseases associated with the occurrence of pathologic cells, particularly tumour ones, in an organism, said method comprising the steps of introducing compounds into blood of an organism, said compounds, particularly iron hydroxychloride, being capable of generating the chemical energy and penetrating into affected cells; saturating blood with oxygen by means of hyperbaric oxygenation, that increases the velocity of oxidation processes and metabolism in the affected cells and formation of interleukins and other activators destroying the cells; acting to the affected cells with electromagnetic fields whose frequency is equal to one of frequencies of their electromagnetic absorption spectrum, is the closest to a frequency calculated for the affected cells and is farthest from a frequency of healthy cells (U.S. Pat. No. 4,994,014, A 61 N 2/02, 1991).

An earlier recommended method for galvanoacoustic stimulation of an organism comprises the step of applying two electrodes of materials having different electrochemical potentials to a region of future action, thereby creating a biogalvanic element. The electrodes of the biogalvanic element are connected to power supply lines of an electrical oscillation generator whose output signal is converted into acoustic oscillations of the same frequency and shape by supplying it to acoustic transducers being placed in an electrode application zone.

As a result of action of the biogalvanic element, the potential difference appears at its electrodes, and is converted by the generator into a sine or cosine voltage in the sound frequency range from 1 to 10 Hz, and then is converted by the transducer into acoustic oscillations of the same frequency and shape. As an internal resistance of biological media tissues of an organism is high, the main portion of a variable component of the generator oscillations is extracted at the electrodes of the biogalvanic element. With this, the frequency of both mechanical and electrical oscillations created in the region of action is determined by a tuning frequency of a generator loop.

This method realises energy produced by the organism itself and does not require external power supply sources, and also does not require the checking of action parameters because they are set and regulated as a type of feedback by the organism itself.

A device for realising said method comprises a sound frequency electrical oscillation generator and a sound oscillation radiator connected thereto and comprising a movable member, for example a membrane, and at least one electric couple consisting of positive and negative electrodes made of electrically conductive materials having different electrochemical potentials, wherein the positive electrode of each couple is connected to a positive power supply line of the generator, and the negative electrode of each couple is connected to a negative power supply line of the generator, and the movable member of the radiator, for example a membrane, is combined with one or several positive and/or negative electrodes, or itself is one of electrodes (Specification to RF Application 94-027,257, A 61 N 23/00, 1996).

To treat vascular diseases of extremities, an action by an electromagnetic field having an intensity of from 200 to 300 Oe and a frequency of from 40 to 68 MHz is combined with the simultaneous impulse barotherapy (USSR Inventor's Certificate 638,339, A 61 N 9/00, 1978).

For the same purpose, it has been proposed to act jointly to an affected extremity with a reduced pressure and an impulsed magnetic field having a direction of field lines along the run of liquid flow in vessels of extremities, a field induction of from 20 to 30 mT and an oscillation frequency of from 20 to 30 Hz, said procedure being implemented in an altitude chamber (USSR Inventor's Certificate 1,475,678, A 61 N 9/00, 1989).

It is reported that a simultaneous action to a tumour with a strike and wave impulse and an impulsed electromagnetic field whose amplitude is greater than a threshold intensity of the field of breaking-down the membranes of tumour cells, but is less than a threshold intensity of the field of breaking-down the membranes of surrounding tissue and organ cells, and allows to increase the effectiveness of sub-cell destruction up to full cessation of tumour growth (RF Patent 2,127,615, A 61 N 1/32, 1999).

It is well known that physiologic effects implied by action of electromagnetic fields to an organism are determined by characteristics of said fields and by parameters of actions to be performed. In this connection, selection of characteristics of the active electromagnetic fields and action modes is key and determines the effectiveness of medical procedures.

In all the above-mentioned prior art methods of medicinal action with electromagnetic fields, selection of field characteristics was carried out:
  empirically, when the characteristics of electromagnetic fields were sorted out based on achievement of a necessary beneficial result;
  by sorting out the characteristics of electromagnetic fields at which an optimum response of blood vessels to an action was achieved in cases when blood flow disturbances were evident and the action was aimed at blood flow normalisation;
  by forming electromagnetic fields coincident in characteristics with that of natural electromagnetic fields of a human body.

In the last-mentioned cases, selection of the measured natural electromagnetic fields was arbitrary, and there are not traced the relationship of active artificial electromagnetic fields and the character of natural electromagnetic fields taking place in a living tissue to be acted.

All the used electromagnetic fields were not uniform in that their uniform action to all the region to be treated was not provided because:
  the designs of devices creating and irradiating the necessary fields for action to organs and tissues of a living organism were not optimised;
  the normalising of geometric characteristics of the electromagnetic fields was not performed;
  the analysis of biological effects in use of non-uniform electromagnetic fields was not performed.

The wide scatter of electromagnetic field parameters and their numeric values taken into account in the prior art methods testifies that absent is a unified approach to selection of active field characteristics and optimisation of their effectiveness.

One inventor of the present invention has established that, despite the wide assortment of produced equipment for electromagnetic therapy and the significant scope of studies associated with responses of organism systems to electromagnetic actions, biophysical grounds for selecting adequate parameters usually are absent, so it was proposed to form the concept of "a bioadequacy of electromagnetic action parameters" relative to the bony and vascular systems as follows: "it is necessary to create such currents in tissues that would be close in shape and geometry to currents occurring in healthy, normally functioning tissues, and would correspond in amplitudes to a patients' sensor sensitivity (Schukin S. I. Apparaty i sistemy dlya bioadekvatnoi electromagnitnoi terapii i activnoi disgnostiki (Devices and Systems for Bioadequate Electromagnetic Therapy and Active Diagnostics). //Medithsinskaya radioelektronika (Medical Radio Electronics).—1999—No 3.—pp. 6–15).

The adequacy of a shape of intrinsic currents, J1(t), and of currents created using an external source, J2(t), will be achieved if $$J1(t)=S \cdot J2(t),$$

where S is a parameter depending upon the sensitivity of sensor systems of a biological object (the degree of activation of the immune system).

Realisation of such the approach, however, causes problems associated with non-uniformity of the conductance and geometry of biological tissues (Schukin S. I. Apparaty i sistemy dlya electromagnitnoi individualnoi terapii i activnoi disgnostiki (Devices and Systems for Electromagnetic Individual Therapy and Active Diagnostics). //Vestnik Moskovskogo Gosudarstvennogo tekhnicheskogo universiteta (Bulletin of the Moscow State Technical University) .—1993.—No. 4.—pp. 9–24).

Said scientific references set forth general concepts of the theory of forming the intrinsic electromagnetic fields by a bony and vascular tissue, and indicate ways of studies that can allow to form artificial electromagnetic fields being the most adequate to natural electromagnetic fields generated by a living biological tissue.

The present invention develops, specifies and slightly simplifies the general statements of theory, that has allowed to state and implement the practical recommendations for normalising biological functions of any living tissues subjected to artificially formed electromagnetic fields.

BRIEF DISCLOSURE OF INVENTION

The main aim of the present invention consists in optimising actions of electromagnetic fields to biological functions of living tissues, that implies improvement of the effectiveness of medicinal procedures and reduction of treatment and rehabilitation periods.

It is known that, in the process of vital activity, intrinsic weak electromagnetic fields are formed in living tissues, defined by intrinsic intensities, recurrence rates and shape of impulses. At the same time, parameters of the intrinsic electromagnetic fields formed in that or other organs and tissues vary with the age, and are distorted when pathologic processes are developed therein.

The Applicant has found that variations of main parameters of electromagnetic fields formed by biological tissues subjected to pathologic changes can be of from 20 to 70% from rated parameter values of the fields formed by living tissues.

The hypothesis placed as the basis of invention is that, if an affected tissue is subjected to actions that will result in restoration of natural characteristics of its electromagnetic field, then, its biological functions will be restored as well.

The essence of the Applicant's proposal is that, for normalising the biological functions of any living tissues and organs, there are the steps of acting to injured tissues with a uniform electromagnetic field directed immediately to a vascular network of the injured tissue while using an electromagnetic field that induces a current being coincident in an impulse recurrence rate and in the impulse shape with and being several orders less in an intensity than respective parameters of a current that is registered during normal functioning of the blood flow system of a respective healthy tissue, checking, during the action process, a response of the vascular system of an organism tissue to said actions, said response being estimated according to the change of blood flow indices, and effecting said action with taking a response intensity into account.

For normalising the biological functions of a tissue, destroyed for some reasons, the characteristics of an intrinsic electromagnetic field of the tissue, such as the impulse recurrence rate, a shape of impulses and an intensity of the electromagnetic field, are preliminary determined in a respective healthy tissue.

Based on obtained information, an artificial electromagnetic field is formed, wherein an impulse recurrence rate and a shape of impulses of this field should be identical to that of an electromagnetic field irradiated by a respective healthy tissue, and its intensity should be several orders less.

The impulse recurrence rate of an intrinsic electromagnetic field of a healthy tissue is usually within from 0.6 to 3.0 Hz.

The shape of impulses of the electromagnetic field of a healthy tissue is bell-like, and it should be reproduced predominantly during formation of external active fields.

As the Applicant has determined, the intrinsic electromagnetic fields in healthy tissues induce currents having a density of from $10^{-3}$ to $10^{-2}$ A/m$^2$, therefore, the external field should induce such the currents in a zone of action, whose density is from $10^{-6}$ to $10^{-4}$ A/m$^2$.

From the studies made it is found that, to solve this problem, the active electromagnetic fields having an impulse recurrence rate of from 0.6 to 3.0 Hz should have an intensity of from 0.5 to 5.0 mT.

As the multi-year Applicant's studies have established that the most significant role in formation of intrinsic electromagnetic fields by living tissues belongs to the blood supply system, then, the direct place for applying external electromagnetic fields should be the vascular network penetrating a biological tissue.

The important condition is the uniformity of an active electromagnetic field. A non-uniform active electromagnetic field cannot have the same effect to all sections of the vascular network, that impacts clinical results of treatment.

Thus, the artificial external electromagnetic fields act mainly and directly to the vascular network of a tissue, thereby having the direct effect on an intrinsic electromagnetic field formed by said tissue.

The principal distinction of the inventive method from prior art methods is that the prior art methods for electromagnetic action to biological tissues had the final aim at normalisation of evidently disturbed blood flow, and the inventive method has the final aim at restoration of parameters of a natural electromagnetic field created by a respective normally functioning living tissue, said parameters being pathologically disturbed not only due to disturbance in the tissue blood supply but for other reasons as well.

At the same time, interrelationship of said indices (the parameters of blood flow and the parameters of an electromagnetic field formed by a biological tissue) in a number of cases, especially associated with evident disturbances in hypodynamics, allows to judge indirectly of normalising the parameters of an electromagnetic field from normalising the parameters of blood flow that can be registered by simpler methods in the process of treatment.

A medicinal procedure comprises the steps of checking a response of the vascular network of a tissue to an effected action according to indices of blood flow, and correcting the action with taking a response intensity into account.

The optimum embodiment includes an action in a mode causing a maximum response of dynamic indices of blood flow, and said response is synchronised with rhythmic parameters of blood flow.

From the intensity of a response to effected actions, it is possible to optimise both parameters of the active electromagnetic field itself and modes of its action, that is, periodicity, duration etc.

The simplest embodiment of the invention includes the step of using an artificially created uniform electromagnetic field that induces a current being coincident in an impulse recurrence rate and a shape of impulses with and being several order less in an amplitude than the respective parameters of a current registered in normal functioning of a respective healthy tissue.

A periodicity of electromagnetic field action is usually established as daily, but other schemes can be used as well.

A duration of a separate procedure and a duration of a treatment cycle depend upon many reasons and are to be determined individually.

In the average, however, a single procedure takes from 15 to 30 minutes, and a treatment cycle is from 10 to 20 procedures.

Said parameters of electromagnetic fields define satisfactory said fields from the standpoint of establishing the adequacy of artificial and natural electromagnetic fields, and the compliance with said parameters ensures the achievement of a respective necessary biological effect.

However, to improve the adequacy of artificial electromagnetic fields to natural ones and, therefore, to improve the effectiveness of treatment, is it further desirable to take into account such a factor taking part in formation of an intrinsic electromagnetic field of organs and tissues, as a frequency of mechanical oscillations of walls of blood vessels that penetrate the organs and tissues.

As the Applicant has found, this frequency has values within from 8.0 to 15.0 Hz.

When forming the active electromagnetic fields, it is necessary to take into account which biological tissue will be acted, and by which blood vessels said tissue will be penetrated. If known is a frequency of mechanical oscillations of walls of respective blood vessels, the value of the mechanical frequency is converted into a value of an electrical frequency, and the last-mentioned is introduced into a characteristic of the active electromagnetic field.

Electromagnetic fields simulating the mechanical oscillations of walls of blood vessels are generally defined by the following parameters: an impulse recurrence rate is from 8.0 to 15.0 Hz, a shape of impulses is sine, an intensity is from 0.5 to 5.0 mT.

This, the optimum embodiment of the present invention uses an artificial uniform electromagnetic field that induces a current being coincident in an impulse recurrence rate and a shape of impulse with and being several orders less in an amplitude than respective parameters registered in normal functioning of a respective healthy tissue, and superposed to said field is a uniform electromagnetic field that induces a current being coincident in characteristics with a current registered in mechanical oscillations of walls of blood vessels penetrating a respective healthy tissue.

To practise the inventive method, it is possible to use at least a device capable of providing the formation of uniform electromagnetic fields that reproduce in characteristics the electromagnetic fields close to intrinsic fields of healthy tissues of an organism.

Such the device should include at least a generator 1, an electromagnetic inductor 2 acting to a biological object 3, a unit 4 for indicating a response of tissue vascular network blood flow indices to an electromagnetic action, a unit 5 for programming parameters of the created electromagnetic field and modes of its action to tissues, and a unit 6 for executing and maintaining the programmed parameters and modes, the generator 1 providing the creation of a bell-like shape of impulses of a current with an impulse recurrence rate in the range from 0.6 to 3.0 Hz.

In particular, the effectiveness of the invention was the most clearly demonstrated in the treatment of especially heavy states and pathologies directly associated with evident or hidden defects of the vascular system, including the treatment of patients having main blood flow disturbances caused by a trauma of a major vessel resulted from an accident, or by a complication after an operation on vessels as a result of their thrombing.

Detailed Disclosure of Invention

The main aim of the present invention consists in optimising actions of electromagnetic fields to biological functions of living tissues, due to a unified universal approach to the formation of active fields.

The final aim of the present invention is to improve the effectiveness and to reduce periods of treatment, postoperative and other types of rehabilitation.

It is known that, in the process of vital activity, intrinsic weak electromagnetic fields are formed in living tissues, defined by intrinsic intensities, impulse recurrence rates and shape of impulses.

Said fields are composed of quasi-constant fields associated with a stable structure of the tissue, an intensity of exchange processes therein, etc., and dynamic fields that occur in the process of deforming the tissues when an organism performs its functions. At the same time, the main physical and chemical effects that give rise to the occurrence of electromagnetic fields, are piezoelectric, electretic and electrocapillary effects.

In the process of vital activity of an organism, that is accompanied with variable dynamic loads, the ratio of quasi-constant and dynamic components of intrinsic electromagnetic fields varies as well (Schukin S. I. Apparaty i sistemy dlya electromagnitnoi individualnoi terapii i activnoi disgnostiki. //Vestnik Moskovskogo Gosudarstvennogo tekhnicheskogo universiteta.—1993.—No 4.—pp. 9–24).

The intrinsic electromagnetic fields occurring in different organs and tissues are different in their characteristics. The characteristics of said fields vary with the age; they depend upon the physiological state of a respective organ or tissue, and are distorted at pathologies and diseases of different types.

One can note that, at the prior art knowledge, it deems to be impossible to reproduce electromagnetic fields fully identical to fields irradiated by biological tissues.

The multi-year Applicant's studies have established that the most significant role in the formation of intrinsic electromagnetic fields by living tissues belongs to the blood supply system: it is the motion of blood through the blood vessels that creates the fields of a determined configuration having particular parameters and characteristics.

It has been stated and fully confirmed the hypothesis that, with the disturbance of biological functions of a living tissue, an electromagnetic field generated by said tissue varies as well, and if actions are effected to this tissue, then, its biological functions will be restored as well.

Variations in main parameters of electromagnetic fields formed by biological tissues subjected to pathologic changes can be of from 20 to 70% from rated parameter values of the fields formed by living tissues.

With this, it was kept in mind that, to restore a natural electromagnetic field of an injured living tissue, it is the most reasonable to provide an action with adequate artificially created electromagnetic fields that, if possible, are the closest in an impulse recurrence rate and a shape of impulses to natural fields of a respective healthy tissue, but have an intensity being several orders less.

With the action of such type, the vascular network of a injured tissue should serve as an application point, said network being predominantly responsible for the formation of an intrinsic electromagnetic field of that or other living tissue.

The essence of the Applicant's proposal is that, for normalising the biological functions of any living tissues and organs, there are the steps of acting to injured tissues with a uniform electromagnetic field directed immediately to a vascular network of the injured tissue while using an electromagnetic field that induces a current being coincident in an impulse recurrence rate and in a shape of impulses with and being several orders less in an intensity than respective parameters of a current that is registered during normal functioning of the blood flow system of a respective healthy tissue, checking, during the action process, a response of the vascular system of an organism tissue to said actions, said response being estimated according to the change of blood flow indices, and effecting said action with taking a response intensity into account.

In order to normalise the biological functions of a tissue for a medicinal purpose, the characteristics of an intrinsic electromagnetic field of the tissue, such as an impulse recurrence rate, a shape of impulses and an intensity of the electromagnetic field, are preliminary determined in a respective healthy tissue.

Based on obtained information, an artificial electromagnetic field is formed, wherein the impulse recurrence rate and the shape of impulses of this field should be identical to that of an electromagnetic field irradiated by a respective healthy tissue, and its intensity should be several orders less.

Such information can be obtained from experimental studies, from literature references or in other way, for example, by calculation.

This information can be obtained using such the prior art methods as Doppler ultrasonography, impedance reoplethysmography, arterial pressure measurements with subsequent processing of obtained data, for example, by digital spectral analysis.

Based on the obtained information, an artificial electromagnetic field is formed, wherein an impulse recurrence rate and a shape of impulses of said field should be the same as that of an electromagnetic field irradiated by a respective healthy tissue, but its intensity should be several orders less.

An impulse recurrence rate of the intrinsic electromagnetic field of a healthy tissue is usually within from 0.6 to 3.0 Hz.

A shape of impulses of the electromagnetic field of a healthy tissue is bell-like, and it should be reproduced generally during formation of external active fields.

As the Applicant has determined, the intrinsic electromagnetic fields in healthy tissues induce currents having a density of from $10^{-3}$ to $10^{-2}$ A/m$^2$.

The intensity of active electromagnetic fields and, therefore, the density of inducted currents should be 100 to 1000 times less than the intensity of intrinsic electromagnetic fields and currents induced thereby and being observed in a healthy tissue.

Therefore, the external field should induce the currents having a density of from $10^{-6}$ to $10^{-4}$ A/m$^2$ in a zone of action.

From the studies made it is found that, to solve this problem, the active electromagnetic fields having an impulse recurrence rate of from 0.6 to 3.0 Hz should have an intensity of from 0.5 to 5.0 mT.

However, depending upon the state of an injured tissue, its localisation, a patient's state of health and other circumstances, the intensity of field can be different as well, that is not a critical parameter.

Generally, reduction of the intensity of the active electromagnetic field against the intensity of the field of a healthy tissue has is aimed at limiting the action by levels providing the information matching with a biological object when the parameters of active electromagnetic fields are essentially less than the intrinsic energy production of biological tissues.

It is theorized that external electromagnetic fields can act to a living organism only having overcame a sensitivity threshold of a biological object, wherein the nature of action depends upon parameters of an active field: at a moderate intensity of a field, its information action to an organism appears; and at a higher intensity, its energetic action appears (Plekhanov G. F. Elektrichestvo, magnetizm, informatsia i zhivye sistemy (Electricity, Magnetism, Information and Living Systems). //Zhivye sistemy v elektromagnitnykh polyakh (Living Systems in Electromagnetic Fields).—Tomsk: Izdatelstvo TGU (Tomsk State University Publishers), 1978.—pp. 3–8).

So called information level of action is defined by influence of electromagnetic fields directly to the functioning process of a biological object, said process being corrected by an active field, and observable biological effects are implied by changes in the biological activity of organs, systems or tissues of a living organism.

The energy level of action causes physical and then biological effects as well, that are induced proper by an active electromagnetic field without an intermediate step of action to the functions of a biological object.

Within the scope of the present invention, the action of electromagnetic fields is directly provided only to the functioning process of a biological living tissue.

The principal distinction of the inventive method from prior art methods is that the prior art methods for electromagnetic action to biological tissues had the final aim at normalisation of evidently disturbed blood flow, and the inventive method has the final aim at restoration of parameters of a natural electromagnetic field created by a respective normally functioning living tissue, that also implies normalisation of biological functions of the respective living tissue disturbed not only due to disturbance of its blood supply but for other reasons as well.

It is another matter that, in the process of restoring the parameters of a natural electromagnetic field, normalisation of the disturbed blood flow takes place as well.

The important condition for implementing the inventive method is an action to a living tissue with a uniform electromagnetic field that as though "trains" and prepares the vascular network of the tissue to formation and restoration of the field characteristics inherent in a healthy tissue.

A non-uniform active electromagnetic field cannot have the same effect to all sections of the vascular network of the tissue and assist in occurrence of adequate responses, thereby hampering the process of recovering normal parameters of the field by the tissue to be acted, said parameters being inherent in a healthy tissue.

The last-mentioned fact is of exclusive importance, because the studies have shown the essential dependence of results upon an amplitude of electromagnetic oscillations. It means that, if the field uniformity condition is essentially not met, that is, if the non-uniformity coefficient is greater that 25%, then, there are body sections that fall into a zone of a constrictor response, other ones that fall into that of a dilator response, and third ones that fall into a zone of relative indifference to an electromagnetic action. This results in competition of vasomotor responses and decreases the total effectiveness of a session of medicinal action.

The uniformity of an active field is provided by the number and geometrical dimensions of used inductors.

In carrying out a medicinal procedure, there are the steps of checking a response of a vascular tissue to the effected action according to blood flow indices, and correcting the action taking a response intensity of into account.

For patients of the allergic and traumatic profiles, it is more preferable to check dynamic indices, for example, a blood flow velocity, stroke and minute blood volumes.

For patients of the cardiac profile, it is better to check rhythmic indices, for example, a pulse rate.

However, it is desirable to check the dynamic and rhythmic indices of blood flow in parallel, and to synchronise the action with the rhythmic indices of blood flow.

In other words, the optimum embodiment of the present invention comprises the step of acting in a mode causing a maximum response of the dynamic indices of blood flow, said action being synchronised with the rhythmic parameters of blood flow.

In doing so, actions can be effected at moments when the indices defining a blood flow rhythm achieve their peak values (that is, a maximum systole or diastole phase), but can lag or lead the moments when the peak values of said indices are achieved.

The indices of blood flow can be checked by any prior art methods, for example, by using impedance rheocardiomonitor systems.

In doing so, the indices of blood flow can be fixed directly in a region which is acted, or in major blood vessels, because the changes of local blood flow in a tissue result in the indices of blood flow in large vessels, and said changes can be detected and registered.

Modes of action to a living tissue with an electromagnetic field are determined by an intensity of a response to the action and are thus optimised.

The optimisation is usually carried out according to the parameters of action causing a maximum response, but such the approach is not obligatory.

Based on the intensity of a response to effected actions, it is possible to optimise both the parameters of an active electromagnetic field itself and its modes of action, that is, a periodicity, a duration, etc.

As noted, natural electromagnetic fields of organs and tissues are subjected to fluctuations within certain limits of values of their parameters.

In this connection, the active electromagnetic fields used to establish both the fact proper of a response and its value, can be defined by a certain scatter of values of their basic parameters that can vary in a smooth manner, in order to establish, in the optimum embodiment, particular parameters of an active electromagnetic field, that give the most clear response in a particular patient.

For this purpose, however, it is also possible to use electromagnetic fields having stable values of basic parameters, said values being varied stepwise.

Establishment of the parameters of a field producing a value of a response, necessary in a particular case, is followed by optimising the modes of action of said normalised field in a similar manner.

The simplest embodiment of the present invention, therefore, comprises the steps of using an artificial uniform electromagnetic field that induces a current being coincident in an impulse recurrence rate and in a shape of impulses with and being several orders less in an intensity than respective parameters of a current that is registered during normal functioning of the blood flow system of a respective healthy tissue.

A periodicity of electromagnetic field action is usually established as daily, but other schemes can be used as well.

A duration of a separate procedure and a duration of a treatment cycle depend upon many reasons and are to be determined individually.

In the average, however, a single procedure takes from 15 to 30 minutes, and a treatment cycle is from 10 to 20 procedures.

Thus, to restore normal characteristics of intrinsic electromagnetic fields of injured organs and tissues, it is necessary at least to act to said organs and bodies with uniform external electromagnetic fields whose impulse recurrence rate, shape of impulses and intensity are matched in the above-mentioned way with characteristics of the electromagnetic fields created by respective healthy organs and tissues.

Said parameters of electromagnetic fields define satisfactory the fields from the standpoint of establishing the adequacy of artificial and natural fields, and the observance of said parameters ensures the achievement of a necessary biological effect.

The parameters of intrinsic electromagnetic fields of healthy tissues (an impulse recurrence rate, a shape of impulses and an intensity) are determined by functioning of the blood flow system that makes the basic contribution to the formation of an electromagnetic field created by biological objects, and their reproduction in characteristics of artificial electromagnetic fields determines the normalisation of field indices of injured tissues.

As experimentally found, however, to improve the adequacy of artificial electromagnetic fields to natural ones, and therefore, to improve the effectiveness of treatment, it is further desirable to take into account such a factor taking part in the formation of an intrinsic electromagnetic field of organs and tissues, as a frequency of mechanical oscillations of walls of blood vessels penetrating the organs and tissues.

This parameter is not associated with indices of the blood flow system and cannot be obtained from such determined indices. To establish it, experimental studies are necessary on a section material.

As the Applicant has found, a frequency of mechanical oscillations of blood vessel walls is within from 8.0 to 15.0 Hz.

When forming artificial acting fields, it is necessary to take into account which biological tissue will be acted and which blood vessels penetrate said tissue.

If a frequency of mechanical oscillations of respective blood vessel walls is known from preliminary trials, the value of the mechanical frequency is converted into a value of an electromagnetic frequency, and the last-mentioned parameter is introduced to a characteristic of an active electromagnetic field.

In other words, the active electromagnetic fields should preferably include a component that induces a current having parameters corresponding to that of a current being registered at mechanical oscillations of walls of blood vessels penetrating a tissue to be acted.

If active electromagnetic fields can be assigned to low-frequency ones because of their impulse recurrence rate, shape of impulses and intensity, then, electromagnetic fields simulating the mechanical oscillation of blood vessel walls should be assigned to sufficiently high-frequency ones.

The last-mentioned fields are predominantly defined by the following parameters: an impulse recurrence rate is from 8.0 to 15.0 Hz, a shape of impulses is sine, an intensity is from 0.5 to 5.0 mT.

In reality, the active fields can be brought into coincidence by any prior art method, particularly, using a wideband generator and an inductor having a filter cutting off the fields with unneeded frequencies, or using a generator that creates electromagnetic fields having only the necessary frequency ranges.

Thus, the optimum embodiment of the present invention uses an artificial electromagnetic field that induces a current being coincident in an impulse recurrence rate and in a shape of impulses with and being several orders less in an intensity than respective parameters registered during normal functioning of a respective healthy tissue subjected to a uniform electromagnetic field that induces a current being coincident in characteristics with a current registered at mechanical oscillations of walls of blood vessels penetrating a respective healthy tissue.

To practise the inventive method, it is possible to use at least a device capable of providing the formation of uniform electromagnetic fields that reproduce in characteristics the electromagnetic fields close to intrinsic fields of healthy tissues of an organism.

Such the device should include at least a generator 1, an electromagnetic inductor 2 acting to a biological object 3, a unit 4 for indicating a response of tissue vascular network blood flow indices to the electromagnetic action, a unit 5 for programming parameters of the created electromagnetic field and modes of its action to tissues, and a unit 6 for executing and maintaining the programmed parameters and modes, the generator 1 providing the creation of a current of a bell-like shape of impulses with an impulse recurrence rate in the range of from 0.6 to 3.0 Hz.

Another embodiment to practise the inventive method can be a device for electromagnetic action to living tissues, in which the electromagnetic inductor 2 is capable of creating a uniform field that induces currents having a bell-like shape impulse recurrence rate of from 0.6 to 3.0 Hz and a sine-shaped impulse recurrence rate of from 8.0 to 15.0 Hz at an intensity of from 0.5 to 5.0 mT, said device comprising a unit 5 for programming parameters of the created electromagnetic field and modes of its action to tissues, and a unit 6 for executing and maintaining the programmed parameters and modes.

The optimum embodiment to practise the inventive method, however, is a device further comprising a pulse volume sensor 7 installed at a biological object 3, and an electromagnetic field impulse synchronisation unit 8 coupled to said sensor.

In the preferred embodiment of the device, the unit 6 for executing and maintaining the programmed parameters and modes comprises a current impulse distributor 9 connected to an output power amplifier 10, wherein coils of the electromagnetic inductor 2 are divided into groups each being directly connected to the output power amplifier 10.

Figure 2:
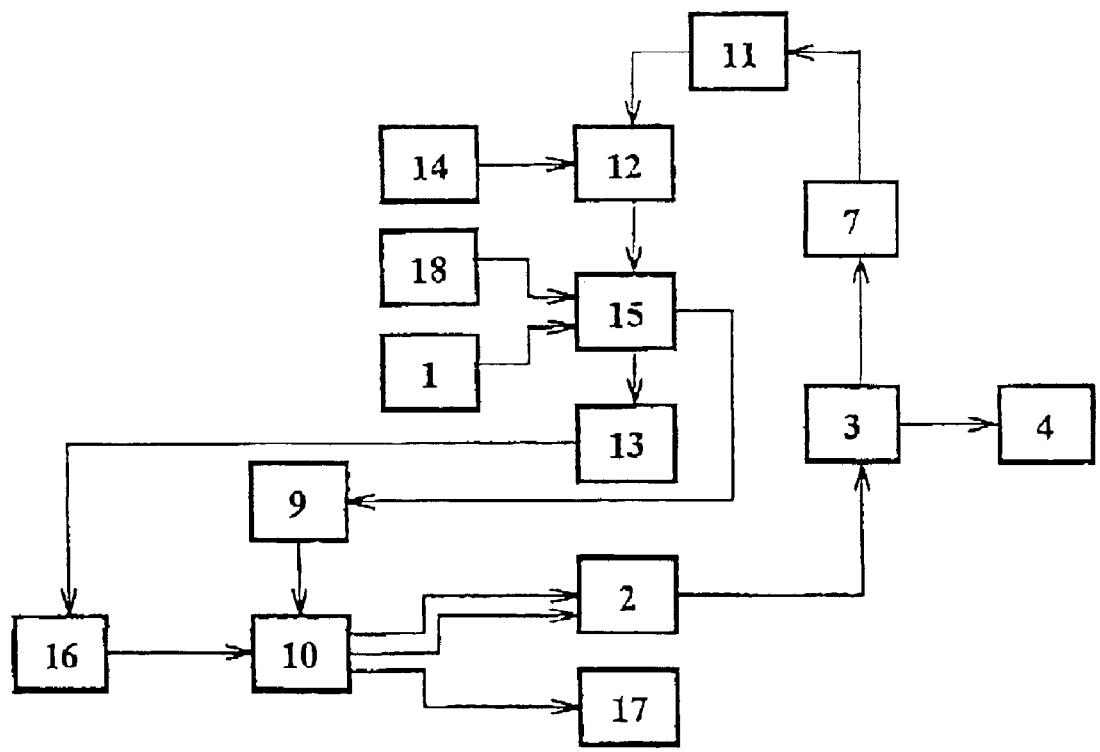

FIG. 1 and FIG. 2 of the drawings enclosed to the Application represent respectively a general block diagram of the inventive device, and one of its embodiments.

FIG. 1 shows a generator 1, an electromagnetic inductor 2 acting to a biological object 3, a unit 4 for indicating a response of tissue vascular network blood flow indices to the electromagnetic action, a unit 5 for programming parameters of the created electromagnetic field and modes of its action to tissues, and a unit 6 for executing and maintaining the programmed parameters and modes.

FIG. 2 shows the preferable embodiment of the disclosed device comprising the generator 1, the electromagnetic inductor 2 acting to a biological object 3, the unit 4 for indicating a response of tissue vascular network blood flow indices to the electromagnetic action, the unit 5 for programming parameters of the created electromagnetic field and modes of its action to tissues, the unit 6 for executing and maintaining the programmed parameters and modes, the pulse volume sensor 7 installed at the biological object 3, and the electromagnetic field impulse synchronisation unit 8 coupled to said sensor.

At the same time, the unit 6 for executing and maintaining the programmed parameters and modes comprises the current impulse distributor 9 connected to the output power amplifier 10, a cardiac contraction frequency signal shaper 11, a delay former 12, and a pulse volume period scale-of-ten-intervals divider 13.

The unit 5 for programming parameters of the created electromagnetic field and modes of its action to tissues comprises a delay former control unit 14, a synchronisation mode control unit 15 and an output current shape determination unit 16.

In addition, the device comprises an output current level indicator 17, a timer 18 and a power supply unit 19 (not shown by convention).

At the beginning of the procedure of action with electromagnetic fields, the generator 1 produces electric impulses whose shape and recurrence rate are set by the unit 5 for programming parameters of the created electromagnetic field and modes of its action to tissues. The impulses arrive at an input of the unit 6 for executing and maintaining the programmed parameters and modes, from whose output the impulses of current arrive at the electromagnetic inductor 2. The electromagnetic inductor 2 converts the impulses of current into an electromagnetic field that acts to the biological object 3. The unit 4 for indicating a response of tissue vascular network blood flow indices to the electromagnetic action allows to check the parameters of blood flow and their changes in time during action of electromagnetic fields, that is used to correct the modes and parameters of action in the unit 5.

In the embodiment of the device shown in FIG. 2, the generator 1, the electromagnetic inductor 2 acting to a biological object 3, the unit 4 for indicating a response of tissue vascular network blood flow indices to the electromagnetic action, operate in a similar manner, and the unit 5 for programming parameters of the created electromagnetic field and modes of its action to tissues comprises the delay former control unit 14, the synchronisation mode control unit 15 and the output current shape determination unit 16. The unit 6 for executing and maintaining the programmed parameters and modes further comprises the current impulse distributor 9 connected to an output power amplifier 10, the cardiac contraction frequency signal shaper 11, the delay former 12, and the pulse volume period scale-of-ten-intervals divider 13.

The delay former control unit 14 allows to determine of a duration of delaying the impulses of an electromagnetic field relative to the systolic front of the pulse volume wave. Modes having a time delay of electromagnetic action impulses relative to hemodynamic cycle phases are of especial interest, and intended to provide said modes are the delay former 12 that produces necessary delays and provides the phase synchronisation of electromagnetic field impulses, and the delay former control unit 14. The delay former control unit 14 provides selection of one of seven fixed delay times and a delay absence mode, "Delay 0", that are set by external controls.

The synchronisation mode control unit 15 allows to set synchronised or automatic modes of electromagnetic action.

To achieve the phase synchronisation of the intrinsic quasi-periodic rhythms of pulse volume and the electromagnetic fields created by the system of inductors, a period of electromagnetic action is divided in the unit 13 into ten equal intervals in time. Actually, a registered current frequency of cardiac contractions is multiplied by ten while keeping the phase ratios for each hemodynamic cycle. Within each of ten intervals, the amplitude of an output current is determined by the output current shape determination unit 16.

The generator 16 produces fixed frequencies in a range of from 0.8 to 12.0 Hz to perform the procedure of electromagnetic action in the non-synchronised automatic mode, said frequencies being useful to perform medicinal procedures of electromagnetic action in traumatology, sport medicine and cosmetology.

The formed impulses of voltage are amplified up to necessary values of the output current in the output power amplifier unit 10 that is a voltage-controlled current source. In doing so, the output current level indicator 17, that is a light-diode matrix, indicates the current really flowing through an operating part, thereby obtaining values of the output current from a current sensor that is a resistor coupled in series to the electromagnetic inductor 2 that is the operating part, and to a load of the output power amplifier 10. At the same time, coils of the electromagnetic inductor 2 are divided into groups each being directly connected to the output power amplifier 10. A group is formed by coils arranged opposite in space, and the groups operate in turn: the impulses of the output current are directed alternatively to one and other group by the impulse distributor unit 9.

Biosynchronisation of electromagnetic action is carried out in accordance with pulse volume cycles using the optical pulse volume sensor 7 operating within the infrared range, said sensor being made as an optocoupler having an open optical channel. The sensor 7 registers pulse volume signals using the principles of photoplethysmographic transducers "for reflection". Registration of photoplethysmographic signals is possible in continuous and impulsed modes of an illuminant. The more complicated technically, impulsed mode of an illuminant allows to obtain the photoplethysmographic signals and impulse volume information being lesser loaded by network loads, interferences and noises, that allows to achieve more stable synchronisation. Continuous (analog) signals arrive at the input of the cardiac contraction frequency signal shaper 11 from the extension pulse volume sensor 7, and said signals are converted into digital control synchronisation impulses in the unit 17. Taken as the beginning of a control synchronisation impulse is the middle of the systolic wave of a photoplethysmogram obtained from the sensor 7. When the pulse sensor is turn off, the operation of the device in the synchronised mode is disabled.

The sequence of using the pulse volume sensor 7 as a part of the currently described embodiment of the device is as follows. Prior to procedures, the device is preliminary turned on for 4 to 5 min, and a necessary time of a procedure as well as necessary shapes, amplitudes, synchronisation modes and a time delay are set using controls. The optoelectronic pulse volume sensor 7 is installed, without any essential pressure, onto a finger of a hand (from the side of palm) or a foot, to an ear lobe or at a surface of a body in locations where major blood vessels are closely placed. In doing so, an operating surface (a "window" of the sensor 7) should contact the skin surface. Prior to install the sensor 7, it is recommended to wash the location of applying the sensor 7 with warm water and soup or to wipe with an alcohol to provide the transparency of optical paths for direct and reflected infrared rays.

After correct setting of the sensor 7, it is necessary to wait for 10 to 25 sec up to appearance of rhythmic indication of a patient's pulse. The criterion of the correct setting is the stable, uniform flashing of the synchronisation indicator, that is coincident with the pulse of the biological object (an indicator "sensor" is designed for this purpose). As the synchronisation sensor 7 is principally sensitive to displacements, then, to obtain the stable synchronous mode of action, a patient should be in a stationary state; the location of the sensor 7 and its connection cord also should be stationary. It is known that the level of surface blood flow is significantly subjected to the effect of external temperature conditions with which the vasomotor reflexes are associated. Therefore, it is necessary first to press a bottom "Start" in order to begin an electromagnetic action; in doing so, the procedure time count begins (in the count-up or count-down mode), and the operating part of the device of the invention, that is, the electromagnetic inductor 2, will create electromagnetic fields corresponding to the selected modes of action.

Simultaneous use of rheoplethysmographic equipment and application of an electromagnetic action is not an obstacle for use of the pulse volume sensor 7 and the synchronisation mode. When registering an electrocardiogram during the sessions of electromagnetic action, however, the essential distortion of registered electrical cardiac signals is possible because of effect of variable electromagnetic fields.

The timer 18 is a procedure clock, is designed for automatic execution of electromagnetic action procedure time intervals up to 60 min by steps of from 5 to 10 min. The timer 18 allows to set a necessary duration (a time doze) of an electromagnetic action procedure and comprises respective controls having digital time indicators. Two seven-segment light-diode indicators, for units and tens of minutes, are intended to determine a current time. Reset of the counter 18 and stop of the described embodiment of the device are carried out automatically upon elapse of the set procedure time, but manual stop is also possible prior to elapse of the electromagnetic action time that was set by the timer.

Basic technical characteristics realised in one embodiment of the inventive device are stated below. The inventive device allows to execute medicinal sessions of the electromagnetic therapy, synchronised according to pulse volume, with the maximum range of a magnetic field induction variation of from 0.5 to 5.0 mT in a geometric centre of the region of action, and with the non-uniformity not greater that 25%. The frequency range of electromagnetic field impulses is from 0.6 to 3.0 Hz and from 8.0 to 15.0 Hz. The typical duration of action is from 20 to 40 min. Used within the inventive device is the extension infrared pulse volume sensor. The time for preparing the inventive device to operation is not greater than 3 min. The inventive device is provided with a special electrical current protection. The overall dimensions are 400×200×400 (the electronic unit), the mass is not greater than 18 kg. The induction amplitude in the operating zone of inductors is up to 5.0±25% mT. The synchronisation accuracy according to the systolic front of pulse volume of a biological object is +25 msec, the automatic and pulse-synchronised modes of operation are available, the field impulse recurrence rate in the automatic mode of operation is 1.0±10% Hz. The shape of impulses is set up, the shape indication has ten amplitude levels.

Practical use of the inventive method and the device designed to implement said method allows to widen the sphere and to improve the effectiveness of use of electromagnetic fields for medicinal purposes, that can result in reduction of treatment periods and in reduction of a duration of the total action to a biological object. The inventive method and device are universal and can be used for therapeutic treatment of injuries of any organs and tissues when there are no contraindications against action of electromagnetic fields.

Especially effective is use of the inventive method in case of heavy states and pathologies associated with evident or hidden defects of the vascular system, but the abilities of the invention are far from being limited thereto. This method can be applied not only for treatment of patients of the traumatic and surgical profile, the method can be used in sport medicine and cosmetology as well.

In particular, the effectiveness of the method was examined in treatment obtain blood flow failures caused by a trauma of a great vessel as a result of an accident (11 observations), or by a complication after operations on vessels as a result of their thrombing (6 observations). In such situations, there are serious neurotrophic complications up to ischemic contractures whose treatment is accompanied with the long rehabilitation, microsurgical plastic operations, and sometimes, with the compelled amputation of an extremity. Results of such the treatment do not satisfy clinical physicians.

Apart from said patient contingent, there were children having carried a "typical" trauma (closed ruptures without peculiarities, contusions) followed by developing complications the basis of which is a vascular factor (non-united fractures, osteomyelitis, ischemic contractures). Sometimes, there is lack of arguments to explain such the complications, because the conduction of such the patients also was not associated with medical errors (incorrect repositioning and immobilisation).

The performed angiographic investigations have shown that the basis of such the complications are vascular deformities that do not manifest themselves in a favourable period and are realised when traumas occur. From 15 patients inspected in this group, 6 children (40%) had the congenital deformities of great vessels. Generally, it manifests in agenesia (2 observations, or 13.5%) or in abnormal development of a great vessel and in absence of one of palm arcs (4 observations, or 27%).

By means of angiography, it was detected that three patients (20% of the group) had ischemic contractures as a result of long obturation of a great vessel lumen by thrombus. In such cases, it is possible to carry out recanalisation of a vessel after a bioadequate electromagnetic action, that results in stimulation of reparative processes in soft tissues without additional surgical interventions. In doing so, the improved development of collaterals first takes place, said collaterals originally providing a regional blood flow and maintenance of reparative processes, and they maintain the necessary level of blood supply in an extremity after recanalisation of a great vessel.

Treatment by an electromagnetic action to patients having failures of regional blood flow through a great vessel was ambulatory. Clinical observation has shown that even children hold the electromagnetic action well. At presence of Volkmann's contracture, the treatment was begun from an action during at least 15 sessions per course, with repetition after month in order to stimulate the peripheral blood flow. The first improvements in the form of sensitivity amplification, occurrence of finger grasps, were noted after 3 to 4 months. The positive clinical dynamics has the stepwise nature. Within half a year after the treatment was started, the skin integument becomes pink and comparable with that of a non-injured extremity, the vascular pattern becomes clear. After 1 to 1.5 years, ischemic events are fully diluted, and the rehabilitation therapy begins, that includes the corrective exercise, massage, mechanotherapy. According to the Applicant's observations, such the treatment has no results without improvement of the regional blood flow up to a sufficient level. It should be noted that the patients' state was significantly improved after 3 to 4 sessions. Ischemic pains were reduced after the first action and disappeared at all after 3 to 4 actions. 10 to 15 sessions were usually sufficient for patients to be acted in the earlier postoperative period.

The effectiveness of the inventive method was estimated from clinic-functional positions of restoration of the regional blood flow and revival of the reparative processes. Considered as an excellent result was dilution of ischemia at earlier stages prior to development of complications, considered as a good result was restoration of the regional blood circulation at later deadlines (more than 6 months), with full restoration of an extremity function after Z-shaped tendinous plastic surgery. A satisfactory result implied the partial restoration of the regional blood flow, that provided maximum effect from a microsurgical plastic operation, an unsatisfactory result implied the full inefficiency of electromagnetic action.

Among the obtained results are: excellent –8 (25%);

good –9 (28%);

satisfactory –15 (47%);

unsatisfactory –0 (0%).

The patients of the present group had no complications associated with use of the inventive method of treatment.

Total results of use of electromagnetic fields in accordance with the inventive method are stated in the Table below.

TABLE

Effectiveness of clinical use of the inventive method in medical practice

| Indications for use<br>1 | Number of patients<br>2 | Effectiveness, %<br>3 |
|---|---|---|
| Prophylactics of slowed-down consolidation of bone tissues after fractures and bone-plastic operations | 259 | 91 |
| Treatment of false joints and fractures not uniting over a long period of time | 178 | 78 |
| Post-traumatic contractures of joints | 115 | 87 |
| Prophylactics of vascular complications after reimplantation of extremities and tissue pieces | 12 | 80 |
| Sluggish-granulating wounds, trophic ulcers | 65 | 87 |
| Osteochondropathies of different localisation | 96 | 88 |
| Dissecting osteochondrosis (König's disease, Panner's disease) | 60 | 91 |
| Prophylactics of traumas of the highest qualification sportsmen during sport assemblages | 51 | 78 |
| Removal of oedema (traumatic and allergic) | 123 | 88 |
| Obliterating diseases of arteries of lower extremities | 43 | 89 |
| Arthritises, arthrosises | 18 | 85 |
| Lymphostasises of different aetiology | 130 | 60 |
| Varicose disease | 36 | 87 |
| Crush syndrome | 12 | 70 |
| Hypertonic disease, I st.-IIA | 19 | 84 |
| Hypertonic disease, III-IIB | 16 | 79 |
| Ulcerative disease of the stomach and duodenum | 11 | 81 |
| Pain syndrome at acute and chronic gastritises, duodenitises, pancreotitises, colitises, adnesitises | 19 | 80 |

The essence of the inventive method is illustrated by the following clinical Examples.

EXAMPLE 1

The patient Sasha is a boy, 11 years old, case report 7594. Diagnosis made: Volkmann's ischemic contracture and post-traumatic pseudoarthrosis. Originally, there was performed the closed repositioning, and the plaster bar was applied. There was observed the marked oedema of the injured extremity. In 3 days after the repositioning, the Elizarov's apparatus was applied. To the end of the first week, the fever has occurred, up to from 38° C. to 39° C. There was performed the specific treatment as to osteomyelitis begun—without effect. After 2.5 months, the sequestrectomy was made as to the functioning fistula. The performed treatment had a low effect, there was formed the false joint of both bones of the right forearm. From the fifth month after the trauma, the ischemic contracture of the right upper extremity is formed.

Taking into account the hard course of the pathological process and extremely low reparative ability, it was decided to carry out the angiographical investigation at which it was found that the radial artery and the deep palmar arch perform their functions in the forearm. The portion of the great vessel channel is absent in the upper third of the radial artery, and the blood flow from the overlying branch goes through collaterals. The division of the brachial artery is observed in the upper third of the forearm (anomaly), wherein the ulnar artery and the surface palmar arch are absent (agenesia). The interbone artery passes in the interbone space, the blood flow in said artery is retrograde and goes via the deep arch. Thus, the extremity trauma took place at the background of the development deformity of forearm vessels. Under such conditions, the anastomosis of transplant vessels is possible only with one of widened return branches of the ulnar artery.

On the seventh month, there has been made the autoplasty of the false joint of right shin fibula fragments using an overbone plate. The plate was rejected, and fistulas were activated. Upon removal of the plate, the Elizarov's apparatus was applied again, and the antibiotherapy was begun.

Within 11 months after trauma, the microsurgical operation for autoplasty with the fibula from the left shin has been made with immobilisation in the Elizarov's apparatus. Within 2 months after operation, the fracture of the transplant has happened, for which the metalosteosynthesis with the Kirschner's pin was made. Unfortunately, it has been led to remove the pin as well after 2.5 months in the context of pin poliomyelitis.

Taking into account the presence of congenital vascular deformities in the right forearm, it has been decided to carry out the course of treatment by electromagnetic actions.

In order to determine optimum modes of an active electromagnetic field, the right forearm region was preliminary acted with a smooth-variable electromagnetic field having the impulse frequency of from 0.6 to 3.0 Hz and an intensity of from 0.5 mT to 5.0 mT. In this case, the shape of impulses was bell-like.

These field parameters were within the values of the natural electromagnetic field created by healthy tissues of upper human extremities, but had the intensity being 1000 times reduced.

At the action with this variable electromagnetic field, a response of the vascular network of forearm tissues to actions was registered.

The fact of action proper and its value were determined as a function of a blood flow change velocity that was measured by Doppler ultrasonography method.

It has been found that, in case of the bell-like shape of impulses, maximum response was observed at the impulse recurrence rate of 1.2 Hz and the intensity of 3.5 mT.

On this basis, said values of parameters were given to the active field used later.

The uniformity of the active field was provided by an extended design of the electromagnetic inductor, that fully encompasses the forearm region.

The periodicity of action with the electromagnetic field was met with the patient's pulse rate and had the delay of 10 seconds from the moment when the action maximum has been achieved.

The duration of one medical procedure was 20 minutes, a single treatment course has included 15 daily procedures. Altogether there were two treatment courses with a pause of 10 days therebetween.

As a result of performed treatment, the fistulas have terminated their functioning, there has been the consolidation of splinters, and the function of the right upper extremity has been improved.

At all the steps of treatment with an electromagnetic action, there was performed the dynamic rheovasographic checking. Prior to treatment, from the side of traumatised extremity, there were noted the drastic suppression of the pulse volume and the significant difficulty of venous outflow, the marked reduction of artery wall elasticity at the kept tone of collateral vessels. From the side of the symmetric uninjured extremity, the pulse volume was slightly elevated at normal tone indices of vessels of all sizes. After the course of treatment, the blood flow asymmetry coefficient of upper extremities has reduced down to 9%, wherein the pulse volume of the right forearm was 10% higher than normal, and the elasticity of the artery vascular wall, the tone of peripheral vessels and the venous outflow were as normal. Clinically, the patient had the improved function of the right hand, the finger grasps have been appeared, the consolidation of splinters occurred without additional surgical intervention.

Upon the end of the course of treatment, the parameters of the intrinsic electromagnetic field of the injured tissue have approached to that of the electromagnetic fields formed by a healthy tissue, while the values of said parameters deviated from normal values up to 65% prior to treatment.

It is possible to make a conclusion that congenital deformities of extremity vessels result in reduction of reparation abilities of traumatised extremities, thereby causing heavy complications that include osteomyelitis and ischemia contractures. The basis for this is in blocking processes of major blood circulation without restoration thereof the reparation processes in the biological tissues are impossible. Under such the conditions, use of operative treatment, including microsurgical treatment, are often ineffective. It is possible to bargain for recovery only upon stable restoration of the regional blood flow and, respectively, upon normalisation of the parameters of natural electromagnetic field in an injured extremity.

The effectiveness of use of the electromagnetic actions in this situation was not evident, but use of the inventive method has confirmed such the possibility.

EXAMPLE 2

The patient Nastia A., 5 years old, report case 4112. The parents have sought for consultation for post-traumatic Volkmann's ischemic contracture of the right upper extremity.

Three months ago, she has fallen from the metal structure at the yard and obtained the closed diacondylar fracture of the right humenus. Because of the significant displacement of splinters and the marked oedema, the skeletal traction was applied. At the third day, in connection with the retained oedema and displacement of splinters, the open repositioning with metalosteosynthesis by Kirshner's pins was made. In operation, it was performed the revision of the shoulder vascular-nervous beam that had no injury, as observed.

Upon the operation, the extremity was in the plaster bar without tight immobilisation. The girl continuously complained for pain in the operated hand and for weakening of the sensitivity. At removal of the plaster bar after 1.5 months, there was detected the stable extensive contracture of the right upper extremity from the elbow joint to the interphalangeel joints of the hand, said contracture quickly gained the nature of ischemic. The hypertrophy of the right forearm was built-up quickly, the integument became waxeous, the sensitivity was fully lost, there was peeling of the skin and trophic ulcers in bends, the local temperature was 27.5° C. at the injured side and 31.8° C. at the uninjured side. Attending physicians had no any explanation of such the neurotrophic failures, and the child was delivered into the clinic for angiographic inspection. The angiograms detected the 8 cm thrombosis of the brachial artery in the lower third, that filly disabled the forearm blood supply.

Originally, the microsurgical reconstructive operation has been proposed to provide angioplasty with the great subcutaneous vein of the femur, but it was discarded by the parents.

It was decided to begin conservative treatment by an electromagnetic action.

To detect optimum modes of action with an electromagnetic field, the shoulder region of the right hand was acted with a stepwise variable electromagnetic field having the impulse rate of from 0.6 Hz to 3.0 Hz and the intensity of from 0.5 mT to 5.0 mT and having the bell-like shape of impulses.

It was found that the uniform electromagnetic field having the impulse frequency of 10.0 Hz, the bell-like shape of impulses and the intensity of 4.0 mT, causes the most clear response of the vascular network of the injured tissue. These parameters determined the parameters of an active filed to be created.

Superposed to the active electromagnetic field was another electromagnetic field having the impulse rate of 12.0 Hz, the sine shape of impulses and the intensity of 4.0 mT.

The second additional electromagnetic field induced the current whose parameters corresponded to that of a current induced by mechanical oscillations of the brachial artery, that takes place in normal functioning of a human upper extremity. Respective values of said parameters were predetermined on an isolated biological material.

The possibility to match said fields was provided by the design of the electromagnetic inductor equipped by necessary filters to cut off electromagnetic fields having other parameters.

The periodicity of action of electromagnetic fields was synchronised with the pulse volume rate and leaded the moment, when the action maximum has been achieved, for 10 seconds.

The duration of one medical procedure was 30 minutes, one course of treatment included 20 procedures that were performed every day.

To estimate the effectiveness of treatment, there were continuous rheovasographic investigations. Prior to treatment, a rheographic signal of the injured extremity was not registered. At the background of treatment, the first clinical improvement has occurred after 1.5 months in the form of appearance of the sensitivity, elevation of the local temperature up to 28.3° C.; the trophic ulcers has healed, the peeling of the skin has terminated, the sweating has occurred in the palm. At this time, the rheograms fixed the sharp reduction in elasticity of the vascular wall, the spasm of peripheral vessels, the sharply hindered venous outflow. The coefficient of asymmetry with the blood flow in the healthy extremity was 72%.

At this period, there were further performed massage sessions, heat procedures, intramuscular administration of the group B vitamins. Therapeutic exercises were absent because they caused the strong pain and were ineffective. However, the pain under loads was estimated as a positive symptom.

Within 6 months after beginning of treatment, the grasp of the first finger has occurred as well as minimum motions in hand joints. The skin temperature was 30.1° C. in the right forearm and 30.2° C. in the left. Rheovasograms noted normalisation of the vascular wall elasticity with maintenance of the spasm of small vessels and sharply reduced venous outflow. The coefficient of asymmetry was 59%. The outflow is absent in test angiograms, but there is the thick network of collateral vessels in the shoulder and forearm, that explains the positive clinical dynamics. Altogether there were 4 treatment courses each including 20 procedures, with pauses of a month therebetween, and with such the treatment, the quick positive dynamics was noted in the form of restoration of all types of finger grasps and full restoration of the skin sensitivity. The local temperature at the right forearm was higher than at the uninjured extremity (33.2° C. and 32.5° C.), as an attestation of intensive regional blood flow. Rheovasograms noted the elevated pulse volume with normalisation of the tome of small vessels and venous outflow. The elasticity of the vascular fall of the uninjured extremity was slightly reduced. The coefficient of asymmetry was 12%. It was noted the restoration of passability of the right brachial artery throughout its extension, with marked collateral vessels.

Clinically, use of the inventive method has provided the marked improvement of the patient's state: the function of the extremity has been fully restored, the right hand does not lag in growth; while few hypertrophy of forearm muscles still takes place, the child actively operates with the hand. The complete unbending, however, is impossible because of cicatrising the long flexor of fingers. Taking into account the success of conservative treatment, it was decided to abandon of the surgical angioplasic operation. Now the question is settled of tendinous plastic operation for complete restoration of motion of the hand fingers.

To that period, the parameter values of the electromagnetic field of the traumatised tissue was not different from that of the electromagnetic field created by a healthy tissue, despite the non-coincidence of the parameter values was of 70% prior to the beginning of treatment by electromagnetic actions.

Effective formation of collateral blood vessels in the shoulder and forearm region, that took place as a result of electromagnetic actions, can be interpreted as an additional confirmation that the positive clinical result is primary implied by normalising the parameters of the intrinsic electromagnetic field of the injured tissue, said normalisation implying subsequent (or simultaneous) restoration of normal blood supply of the injured tissue as well.

EXAMPLE 3

The patient Kolya is a boy, 10 years old; clinical diagnosis: syndrome of long squeezing of the lower extremities, acute renal failure.

The child located under fragments of a building for 5 hours and had no medical assistance for 10 hours since the catastrophe occurred.

The condition as admitted is grave, the patient is conscious, the skin integument is pale, the respiration is listened at both sides, râles are not determined, heart sounds are muffled, the tachicardia is up to 130 beats per minute.

The abdomen is soft, painless. Does not excrete urine.

Locally: upper extremities are oedematous, tissues are stressed, the skin is of a pale-pink colour with red spots in the region of shin, foot and fingers. In the region of front and back surfaces of both shins, the skin is of a blue-violet colour.

During the first three days since the child was admitted to the clinic, the intensive intravenous infusion therapy for normalisation of homeostasis and dehydration of the organism, hypebaric oxygenation, and hemosorption were begun and performed.

There were no improvements noted. In the day when the child has come to the clinic, it was performed the radio isotope investigation of blood flow in both lower extremities. The lowering of blood flow was noted in the lower third of shin of both lower extremities.

There was no improvement in common condition of the child during the first day of his treatment, the child did not urinate. There were marked anaemia and toxicosis.

After repeated radio isotope investigation at the next day, it was detected the increase of the lowered blood supply zone of soft tissues in the region of the lower third of both extremities.

In the third day of residence, the common condition of the child is very grave, the intoxication is maintained, there are marked anaemia and disordered urine outflow.

The performed skin thermometry and rheovasographic investigations of extremities have shown: the marked reduction of arterial blood filling, especially from the side of hips and in the right shin; the deceleration of venous outflow and the peripheral vasotilation in the left leg; the peripheral vasoconstriction in the right leg; the decrease in an average velocity of blood filling and the increase in a relative index of the vascular wall elasticity.

It was decided to carry out the course of electromagnetic actions.

The determination of parameters of a natural electromagnetic field, created by tissues of the injured lower extremities, showed that the variation of basic parameters of said field from the parameters of the field generated by healthy tissues is of 60 to 65%.

It was preliminary found that the optimum response of the vascular network to the action of an artificial adequate electromagnetic field is achieved when the impulse recurrence rate of the active field is 0.8 Hz, the field intensity is 3.0 mT, and the shape of impulses is bell-like. Superposed to this active field was an additional electromagnetic field having the intensity of 4.5 mT and inducing a current that has the impulse recurrence rate of 12.0 Hz and the sine shape of impulses.

The periodicity of the combined field was synchronised with the blood filling rate.

After the first session of electromagnetic actions to the right hip and to the upper third of the right shin using the apparatus capable of generating a uniform electromagnetic field with said parameters, the repeated skin integument thermometry and rheovasography were performed. The marked change of the skin temperature was not noted, but there were noted the increase in the intensity of arterial blood flow and the average velocity of blood filling, the improvement in the venous outflow, the reduction of the arterial vessel spasm.

After the second session of the electromagnetic action, the tendency was noted from rheovasographic data to increase the blood flow intensity and to decrease the arterial vessel spasm.

After the third session of the electromagnetic action, some decrease of oedema of the right lower extremity was noted, while the boundaries of skin hyperaemia were the same.

During all this period, the treatment procedures of hyperbaric oxygenation and hemodialysis were continued as well.

The child was a bit better, the urine excretion has increased up to 250 ml of urine. The condition of lower extremities has improved, the sensitivity zones have widened, the hyperaemia zones have decreased.

After the fourth session of the action with electromagnetic fields, the patient's condition has further improved, with decrease of the area of the hyperaemia zone in the region of lower extremities. There was evident decrease of soft tissue oedema.

Altogether there were 10 sessions of the action with electromagnetic fields, said sessions were carried out daily, each session had the duration of 30 minutes.

Within two weeks after beginning of the action with electromagnetic fields, the marked improvement is noted in the condition of the child, the positive dynamics in improvement blood indices is observed, the skin integument in the region of lower extremities has taken the normal colouring, and the oedema has disappeared. The daily amount of urine has increased up to 1500 ml per day, with normal transparency and colour indices.

At said moment, the variation of parameters of the electromagnetic field generated by lower extremity tissues of the child from parameters of the field created by healthy tissues, was not greater than 5–10%.

The child was discharged to complete the cure.

When estimating the effectiveness of electromagnetic actions, apart from clinical observations, there were used the techniques of peripheral impedance rheovasography, local thermography, radio isotope investigations, rentgenography, computer thomography, ultrasonic flowmetry, biochemical investigations of blood and acid-base equilibrium parameters.

It is evident that, the effectiveness of conservative restoration of major blood flow in an extremity, said effectiveness being implied by normalisation of the parameters of the intrinsic electromagnetic field of the injured tissue, in a number of cases can allow to abandon reconstructive angioplastic operations. In doing so, the volume of surgical treatment of complications resulted from the carried ischemia is significantly reduced.

Thus, it was proved the effectiveness of use of the inventive method of electromagnetic actions in traumatic practice for stimulating the reparative processes when a traumatic injury is complicated by hidden hemodynamic defects, that widens the abilities and sphere of use of electromagnetic fields in the art of practical medicine.

What is claimed is:

1. A method for normalising biological functions of living tissues by action of an electromagnetic field to injured tissues comprising the steps of: imposing a uniform electromagnetic field upon the injured tissue that induces a current coincident in an impulse recurrence rate and in an impulse shape with and being several orders less in an intensity than respective parameters of a current that is registered during normal functioning of a respective healthy tissue, checking, during the action process, response of the vascular system of said tissue to said actions, said response being estimated according to the change of blood flow indices.

2. The method according to claim 1, wherein said action is provided by said uniform electrical field having an intensity of from 0.5 to 5.0 mTl, which induces a current with impulse repetition frequency of 0.6 to 3.0 Hz and a bell-like shape of impulses.

3. The method according to claim 2, wherein the action is effected in a mode causing a maximum response of the synamic indices of blood flow, and synchronised with rhythmic parameters of blood flow.

4. The method according to claim 1, wherein an additional action is provided to the injured tissues by an electromagnetic field having an intensity of from 0.5 to 5.0 mTl, which induces a current with impulse repetition frequency of 8.0 to 15 Hz and having a sine shape of impulses.

5. A device for electromagnetic action to living tissues, comprising a generator, an electromagnetic inductor acting to a biological object, characterised in that said device further comprises a unit for indicating a response of tissue vascular network blood flow indices to the electromagnetic action, a unit for programming parameters of the created electromagnetic field and modes of its action to tissues, and a unit for executing and maintaining the programmed parameters and modes, the generator providing the creation of a current having a bell-like shape of impulses with an impulse recurrence rate in the range of from 0.6 to 3.0 Hz.

6. The device according to claim 5, wherein said device further comprises a pulse volume sensor adapted to be installed at a biological object, and an electromagnetic field impulse synchronisation unit coupled to said sensor.

7. The device according to claim 5, wherein the unit for executing and maintaining the programmed parameters and modes of action comprises a current impulse distributor connected to an output power amplifier, wherein coils of the electromagnetic inductor are divided into groups each being directly connected to the output power amplifier.

8. A device for electromagnetic action to living tissues, comprising a generator, an electromagnetic inductor acting to a biological object, characterised in that the electromagnetic inductor is creating a uniform field that induces currents having a bell-like impulse recurrence rate of from 0.6 to 3.0 Hz and a sine-shaped impulse recurrence rate of from 8.0 to 15.0 Hz at an intensity of from 0.5 to 5.0 mT, said device comprising a unit for indicating a response of tissue vascular network blood flow indices to the electromagnetic action, a unit for programming parameters of the created electromagnetic field and modes of its action to tissues, and a unit for executing and maintaining the programmed parameters and modes.

9. The device according to claim 8, wherein said device further comprises a pulse volume sensor adapted to be installed at a biological object, and an electromagnetic field impulse synchronisation unit coupled to said sensor.

10. The device according to claim 8, wherein the unit for executing and maintaining the programmed parameters and modes of action comprises a current impulse distributor connected to an output power amplifier, wherein coils of the electromagnetic inductor are divided into groups each being directly connected to the output power amplifier.

* * * * *